(12) United States Patent
Schussler et al.

(10) Patent No.: US 6,319,949 B1
(45) Date of Patent: *Nov. 20, 2001

(54) PESTICIDAL SPRAYS

(75) Inventors: Jeffrey R. Schussler, Chardon; Robert E. Moser, Concord; Kevin E. Crosby, Painesville, all of OH (US); John R. Washington, La Lima Nueva (HN)

(73) Assignee: Syngenta Limited (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/740,834

(22) Filed: Nov. 4, 1996

Related U.S. Application Data

(60) Provisional application No. 60/021,536, filed on Jul. 11, 1996.

(51) Int. Cl.$^7$ .......................... A01N 25/32; A01N 27/00; A01N 37/34; A01N 37/44; A01N 37/46; A01N 43/52; A01N 43/653; A01N 47/12

(52) U.S. Cl. .......................... 514/520; 514/256; 514/269; 514/359; 514/365; 514/383; 514/388; 514/389; 514/391; 514/394; 514/395; 514/396; 514/399; 514/400; 514/479; 514/483; 514/521; 514/532; 514/538; 514/539; 514/543; 514/640; 514/617; 514/724; 514/739; 514/762; 514/763; 514/764; 514/765; 514/772; 514/789; 514/922; 514/974; 424/406; 424/DIG. 8

(58) Field of Search .................. 514/520, 974, 514/762, 724, 739, 256, 269, 359, 365, 383, 388, 389, 391, 394–396, 399, 400, 479, 483, 521, 532, 538, 539, 543, 640, 617, 763, 764, 765, 772, 789, 922; 424/406, DIG. 8

(56) References Cited

U.S. PATENT DOCUMENTS

| | | | |
|---|---|---|---|
| 2,030,093 | * 2/1936 | Bousquet et al. | 514/724 |
| 3,290,353 | * 12/1966 | Battershell et al. | 558/419 |
| 3,778,509 | * 12/1973 | Lewis | 514/724 |
| 3,833,736 | * 9/1974 | Frick et al. | 514/724 |
| 3,869,494 | 3/1975 | Battershell | 260/465 |
| 4,078,070 | 3/1978 | Albrecht et al. | 424/273 |
| 4,105,775 | 8/1978 | Albreecht et al. | 424/273 |
| 4,238,219 | 12/1980 | Holm et al. | 71/86 |
| 4,242,356 | 12/1980 | Hasegawa et al. | 424/279 |
| 4,297,258 | 10/1981 | Long, Jr. | 260/29.6 |
| 4,302,467 | 11/1981 | Hasegawa et al. | 424/270 |
| 4,303,668 | 12/1981 | Hasegawa et al. | 424/279 |
| 4,329,277 | 5/1982 | Murphy | 523/122 |
| 4,378,355 | 3/1983 | Nakagawa et al. | 424/230 |
| 4,584,309 | 4/1986 | Ishiguri et al. | 514/383 |
| 4,785,013 | 11/1988 | Margossian | 514/391 |
| 4,847,285 | 7/1989 | Haberle et al. | 514/425 |
| 4,959,388 | 9/1990 | Wilde | 514/479 |
| 4,987,142 | 1/1991 | Tocker | 514/383 |
| 4,990,342 | 2/1991 | Wilde | 424/635 |
| 5,009,937 | 4/1991 | West et al. | 427/440 |
| 5,013,746 | 5/1991 | Van Gestel et al. | 514/365 |
| 5,223,524 | 6/1993 | Valcke | 514/383 |
| 5,250,559 | 10/1993 | Mittermeier et al. | 514/383 |
| 5,260,326 | 11/1993 | Sauter et al. | 514/383 |
| 5,294,640 | 3/1994 | Leinen et al. | 514/525 |
| 5,317,027 | 5/1994 | Sauter et al. | 514/399 |
| 5,380,484 | 1/1995 | Woods et al. | 422/6 |
| 5,385,750 | * 1/1995 | Aleksejczyk et al. | 427/4 |
| 5,389,665 | 2/1995 | Faers et al. | 514/399 |
| 5,397,795 | 3/1995 | Valcke | 514/383 |
| 5,399,579 | 3/1995 | Sauter et al. | 514/383 |
| 5,484,779 | 1/1996 | Sauter et al. | 514/63 |
| 5,496,568 | 3/1996 | Winston | 424/717 |

OTHER PUBLICATIONS

Backman "Fungicide Formulation: Reltaionship to Biological Acitivty", Am Rev. Phytopathol. (1978), 211–237.

Steurbaut "The Influence of Nonionic Surfactants on the Penetration and Transport of Systemic Fungicides in Plants" Adjuvants and Agrochemicals Chapter 10, vol. 1, 93–103 (1984).

Steurbaut "Improvement of Fungicide Performance by the Addition of Surfactants tot he Formulations" Med. Fac. Landbouww, Rijksuniv. Gent., 1989, 207–218.

Sotel "Evaluation of Systemic Fungicides and Mineral Oil Adjuvants for the Control of Mal Secco Disease of Lemon Plants "Phytopathology 62: 1007–1013, 1972.

Calpouzos "Oils", Fungicides an Advanced Treatise, Chapter 8, 1969, 367–393.

Krenek, M.R. et al., "Factors affecting the Phytotoxicity of Solvents used in Pesticide formulations," Pestic. Sci. Biotechnolo., Proc. Int. Congr. Pestic. Chem., 6$^{th}$ 1986, pp. 287–290, Published 1987.*

Backman, P.A., "Effects of Spray Adjuvants on deposition and retention of the fungicide chlorothalonil on Soybean Leaf Surfaces," Phytopathology, vol. 75, No. 10, 1985, p. 1175.*

Chemical Abstracts 112: 193744 (1990).*

\* cited by examiner

*Primary Examiner*—John Pak
(74) *Attorney, Agent, or Firm*—Hale and Dorr LLP

(57) ABSTRACT

A method for preventing fungal diseases in crops which comprises the steps of: (a) applying to a crop an aqueous or a non-aqueous spray composition which includes a pesticide and a spray adjuvant including a solvent and an emulsifier, wherein the solvent is a mixture of aliphatic hydrocarbons having a distillation range of about 520 to 600° F. and an aromatic content of about 1% or less, or the solvent is a single or combination of $C_6$–$C_{18}$ fatty alcohol(s); and (b) applying chlorothalonil to the crop previously to, simultaneously with, or subsequently to the application of the aqueous spray composition, wherein phytotoxicity associated with the application of chlorothalonil is reduced or eliminated.

24 Claims, 2 Drawing Sheets

PESTICIDAL SPRAYS

Figure 1:
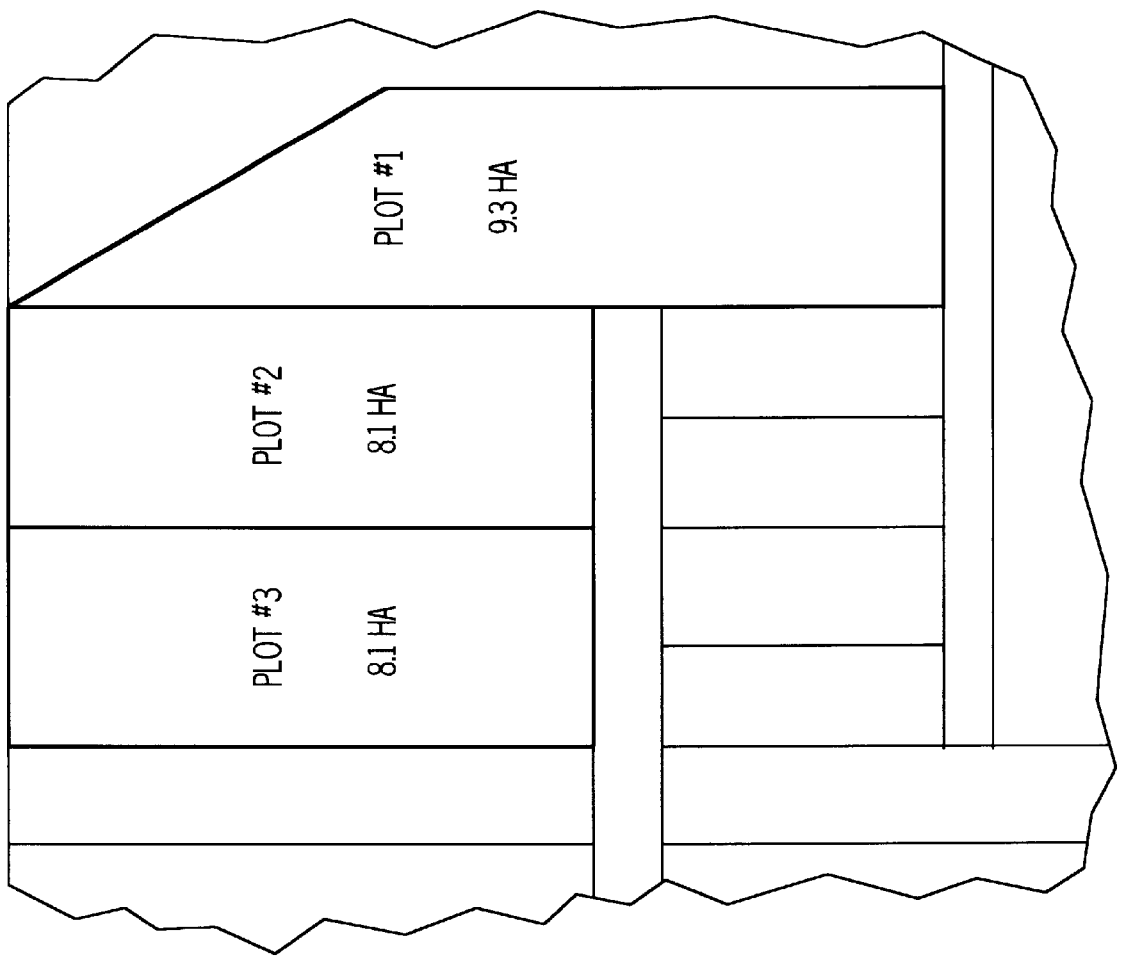

This application claims priority of provisional application Ser. No. 60/021,536, filed Jul. 11, 1996.

BACKGROUND OF THE INVENTION

The present invention relates to a spray adjuvant useful in the application of pesticides for treating crops which alleviates phytotoxicity associated with chlorothalonil and to a method for preventing fungal diseases employing such spray adjuvant in combination with pesticides. The invention more particularly relates to a method for preventing fungal disease in crops such as banana crops in which a spray adjuvant is used which provides satisfactory uptake of a systemic fungicide such as propiconazole but minimizes the phytotoxicity of a contact fungicide such as chlorothalonil.

Systemic fungicides and other systemic pesticides are commonly applied to crops as an aqueous spray containing spray adjuvants such as surfactants and emulsified agricultural crop oils which insure that the pesticide is deposited as a droplet which wets the leaf and is retained on the leaf of the plant so that the pesticide can be absorbed. For example, banana spray oils (BSO), commonly used in combination with systemic fungicides in banana production, deposit an oily residue on the leaf surface which promotes the uptake of the systemic fungicide.

To reduce developing resistance to any particular pesticide, it is common practice to rotate pesticides. In some areas of the world, it is a common practice of growers to sequentially or simultaneously treat the crops with a systemic fungicide cocktail containing BSO and with chlorothalonil. However, an antagonistic response has been observed involving the oil and chlorothalonil resulting in unacceptable necrosis of leaf tissue.

SUMMARY OF THE INVENTION

In accordance with the present invention, an effective spray adjuvant in combination with a pesticide is employed that alleviates phytotoxic interaction often associated with chlorothalonil applications. Thus, treatment programs in which the two types of fungicides are used sequentially, or in combination, can be utilized to provide better overall disease control and to retard the development of disease resistance to systemic fungicides. In accordance with one embodiment of this invention, a combination of solvents and emulsifiers is provided which stimulates the foliar uptake of systemic fungicides and other pesticides without phytotoxic interactions associated with subsequent, concurrent or previous chlorothalonil applications. The solvent and emulsifier are typically used as a tank-mix adjuvant which can be added to commercial pesticidal formulations for liquid application to foliage of crops such as bananas, or they can be added by the manufacturer directly to the commercial formulation. The invention may also be used to enhance fungicide uptake in crops other than bananas, e.g., peanut crops, cereal crops, vegetable crops, fruit crops, forage crops, and tree crops. Similarly, this invention may be used to enhance the efficacy of other pesticides including herbicides and insecticides.

One manifestation of the invention is a method for preventing fungal disease in crops which comprises the steps of:

(a) applying to a crop an aqueous spray composition which includes a pesticide and an emulsifier-solvent combination wherein the solvent is a mixture of aliphatic hydrocarbons having a distillation range, at ambient pressure, of about 520 to 600° F. and an aromatic content of about 1% by weight or less, or the solvent is a single or combination of $C_6$–$C_{18}$ fatty alcohol(s) preferably $C_{10}$–$C_{14}$ fatty alcohols; and (b) applying chlorothalonil to the crop, wherein any phytotoxicity associated with the application of chlorothalonil is reduced or eliminated. The chlorothalonil can be applied to the crop prior to, simultaneously with, or subsequent to the application of the aqueous spray composition. In addition to being a method for treating crops, those skilled in the art will appreciate that the invention also provides spray formulations and adjuvants formulations.

Another manifestation of the invention is a method for preventing fungal disease in crop which comprises the steps of:

(a) applying to a crop a non-aqueous based spray composition which includes a pesticide and a solvent, wherein the solvent is a mixture of aliphatic hydrocarbons having a distillation range of about 520 to 600° F. and an aromatic content of about 1% by weight or less, or the solvent is a single or combination of $C_6$–$C_{18}$ fatty alcohol(s); and (b) apply chlorothalonil to the crop previously to, simultaneously with, or subsequently to the application of the non-aqueous spray composition, wherein phytotoxicity associated with the application of chlorothalonil is reduced or eliminated.

BRIEF DESCRIPTION OF THE DRAWINGS

FIG. 1 shows the location of three experimental noncommercial plots adjacent a commercial banana plantation in Honduras.

FIG. 2 is a graph showing mean YLA data on each rating date for three treatments.

DETAILED DESCRIPTION OF THE INVENTION

The invention is based on the identification of certain aliphatic hydrocarbons and fatty alcohols which can be substituted for agricultural crop oils, including BSO, in conventional pesticidal formulations and which stimulate the uptake of the systemic fungicide (or the efficacy of other pesticides) without producing phytotoxicity upon the application of chlorothalonil. The term "pesticide" as used herein includes fungicides, herbicides and insecticides/acaricides.

In a preferred embodiment, the systemic pesticide is propiconazole, but the method of the invention can also be used with other triazole fungicides such as fenbuconazole, hexaconazol, epoxiconazol or tebuconazole, and other systemic fungicides and chemical classes known in the art; e.g., benzimidazoles such as benomyl, thiabendazole, and the like; fungicidal dicarboximides such as iprodione, etc.; thiophanatemethyl and the like; fungicidal phenyl amides such as metalaxyl, mefenoxame, etc.; fungicidal strobiluranes (,i.e., strobiurin derivative) such as azoxystrobin, kresoxim-methyl, etc.; fungicidal pyrimidines such as fenarimol, etc.; and fungicidal imidazoles such as imazilil, etc. In addition to chlorothalonil, it is also anticipated that the spray adjuvant may be useful in reducing the phytotoxicity associated with the application of other contact pesticides which exhibit phytotoxicity such as tridemorph, a morpholine-type fungicide.

While not desiring to be bound, it is believed that the spray adjuvants used in the invention exploit the solubility differences in the pesticides. For example, in the case of propiconazole and chlorothalonil, propiconazole is more soluble in the solvent and is readily taken up by the plant but the chlorothalonil is not. As a result, essentially no phytotoxicity is observed when chlorothalonil is applied in conjunction with the adjuvants.

The hydrocarbon solvent in the aqueous spray adjuvant is a mixture of aliphatic hydrocarbons having a distillation range of about 520 to 600° F. and an aromatic content of about 1% by weight or less. Typically, the hydrocarbon solvent is a hydrotreated aliphatic petroleum distillate derived from paraffinic or naphthenic crudes, having a distillation range of about 538 to 599° F. Preferably, the aliphatic hydrocarbon is an isoparaffinic and naphthenic mixture having a distillation range of about 523 to 592° F. Representative examples of the aforementioned aliphatic hydrocarbon include Isopar V, Exxsol CP 130 and Exxsol D130 available from Exxon Corp.

The fatty alcohols useful in the present invention include those having a carbon content of $C_6$ to $C_{18}$, typically the fatty alcohol has a carbon content of $C_{10}$ to $C_{18}$, and preferably the fatty alcohol is a $C_{10}$–$C_{16}$ fatty alcohol distilling in the range of about 480 to 580° F. In a preferred aspect of the invention, the fatty alcohol is dodecanol ($C_{12}$), tetradecanol ($C_{14}$) or mixtures thereof. Typically, the fatty alcohol contains a majority of dodecanol and preferably the mixture contains about 65 to 75% by volume dodecanol and about 25 to 35% by volume tetradecanol. Representative examples of the fatty alcohols include lauryl alcohol ($C_{12}$), e.g., EPAL 12 available from Albemerle Corp., and myristyl alcohol ($C_{14}$). Other fatty alcohols useful in the invention are available from Henkel Corporation.

In addition to the solvent, the adjuvant also contains an emulsifier system. The emulsifier is selected from those which do not detract from the differential uptake that is achieved through the use of the identified solvents. One useful emulsifier is one or more nonionic emulsifier components, alone or in combination with other alcohols, esters, alkyl ethoxylates and resins. Many of the emulsifiers conventionally used in agricultural spray adjuvants can be used in the invention, the preferred emulsifier is Adsee ME 722, which is a mixture of surface agents and emulsifiers (a nonionic emulsifier, alkoxylated resin and methyl soyate) and is commercially available from Witco Chemical Co. The concentration of the emulsifier in the solvent in the spray adjuvant can vary over a broad range but typically is about 2 to 10% by weight. The amount of emulsifier in the adjuvant is preferably limited so as not to offset the benefit of reduced phytotoxicity associated with using the aforementioned solvents in accordance with the invention.

In formulating sprays for application to crops, the adjuvant is tank-mixed with the commercial formulation of the systemic fungicide in an aqueous suspension. The adjuvant is used in an amount of about 2 to 20% by volume. As an illustration of the use of the adjuvants, Exxsol D130 is mixed with Adsee ME722 in a 50:1 ratio (solvent:emulsifier) and the mix is combined with the propiconazole formulation (100 g ai/ha) and water in an amount of about 10 to 20% total volume, and EPAL 12 is mixed with Adsee ME 722 in a ratio of 10:1 and the mix is combined with propiconazole formulated to the manufacturer's specifications and water in an amount of about 5 to 10% of total volume. Those skilled in the art will recognize that the amount of the spray adjuvant can be adjusted based on the spraying equipment and the spray conditions used, the solubility of the pesticide in the adjuvant, the application rate and volume.

Hereinabove, the invention has been described as an aqueous spray. However, the invention also finds application to non-aqueous, oil-based pesticidal sprays. In accordance with this embodiment of the invention, the aforementioned solvents are used in place of a solvent like BSO to formulate oil-based sprays that contain chlorothalonil or are used in conjunction with chlorothalonil or other pesticides which exhibit phytotoxicity when they are applied in conjunction with other solvents. Thus, in accordance with this embodiment of the invention, a method is provided which comprises the steps of:

(a) applying to a crop an oil or solvent-based spray composition which includes a pesticide and a solvent wherein the solvent is a mixture of aliphatic hydrocarbons having a distillation range of about 520 to 600° F. and an aromatic content of about 1% by weight or less, or the solvent is one or a combination of $C_6$–$C_{18}$ fatty alcohol(s) and (b) applying chlorothalonil to the crop, wherein phytotoxicity associated with the application of chlorothalonil is reduced or eliminated. The chlorothalonil can be applied to the crop prior to, simultaneously with, or subsequent to the application of the oil or solvent-based spray composition.

The hydrocarbon solvent in the non-aqueous or oil-based spray adjuvant is a mixture of aliphatic hydrocarbons having a distillation range of about 520 to 600° F. and an aromatic content of about 1% by weight or less. Typically, the hydrocarbon solvent is a hydrotreated aliphatic petroleum distillate derived from paraffinic or naphthenic crudes, having a distillation range of about 538 to 599° F. Preferably, the aliphatic hydrocarbon is an isoparaffinic and naphthenic mixture having a distillation range of about 523 to 592° F. Representative examples of the aforementioned aliphatic hydrocarbon include Isopar V, Exxsol CP 130 and Exxsol D130 available from Exxon Corp.

The fatty alcohols useful in the present invention include those having a carbon content of $C_6$ to $C_{18}$, typically the fatty alcohol has a carbon content of $C_{10}$ to $C_{18}$, and preferably the fatty alcohol is a $C_{10}$–$C_{16}$ fatty alcohol distilling in the range of about 480 to 580° F. In a preferred aspect of the invention, the fatty alcohol is dodecanol ($C_{12}$), tetradecanol ($C_{14}$) or mixtures thereof. Typically, the fatty alcohol contains a majority of dodecanol and preferably the mixture contains about 65 to 75% by volume dodecanol and about 25 to 35% by volume tetradecanol. Representative examples of the fatty alcohols include lauryl alcohol ($C_{12}$), e.g., EPAL 12 available from Albemerle Corp., and myristyl alcohol ($C_{14}$). Other fatty alcohols useful in the invention are available from Henkel Corporation.

This method is applicable to the application of the same classes of pesticides previously discussed with respect to the use of aqueous sprays. Solvent-based sprays are formulated in a conventional manner at conventional concentrations. Typically, the solvent is used in the solvent-based composition in an amount of about 80 to 96% by volume.

EXAMPLE

Over 150 different test substances were tank-mixed with chlorothalonil (Bravo 720) and applied to banana plants grown in a greenhouse. After several days, plants were observed for the appearance of phytotoxic responses. Typically, these responses ranged from mild chlorosis to severe necrosis of the entire leaf lamina. Currently used commercial banana spray oils (SprayTex M, Orchex 692, Sunspray 11 E) were included as standards for comparison. When tank-mixed with Bravo, these BSO's typically caused a phytotoxicity rating of about 20–40% (0–100 scale) to the treated leaves. Test substances caused phytotoxicity ratings ranging from 0 to 80%. Test substances which caused less than 10% damage were considered significantly better than BSO and were advanced to the second level of testing. The results are shown in Table 1 below.

TABLE 1

| Treatment Description | Phytotoxicity Rating (0–100) |
|---|---|
| Untreated Control | 0 |
| B Alone | 0 |
| B + Isopar V 25% + A (0.5%) | 7 |
| B + Exxol CP-130 25% + A (0.5%) | 15 |
| B + Exxol D-130 25% + (05%) | 8 |
| B + Sunspray 11E 25% + A (0.5%) | 25 |
| B + Banol 25% + A (0.5%) | 25 |
| B + Orchex 692 25% + A (0.5%) | 24 |
| B + SprayTex M 25% + A (0.5%) | 23 |
| B + Epal 12 5% + A (0.5) | 13 |
| B + Epal 12/70 + A (0.5) | 9 |

A = Adsee ME-722
B = Bravo 720 at 2 l/ha

The objective of the second level of testing was to compare the ability of test substances to enhance the movement of propiconazole (Tilt, Ciba-Geigy) into banana leaves. Efficacy of this systemic fungicide is related to the amount of active ingredient which moves into the leaves where it expresses its fungicidal effect. An uptake assay system utilizing $^{14}$C-propiconazole was developed to measure the effect of the test substances on Tilt uptake in banana leaves. Very few test substances were as effective as BSO's in enhancing the uptake of Tilt. The most promising candidates were advanced to a third level of testing where $^{14}$C-propiconazole uptake was evaluated in a commercial tank-mix. Several combinations were found to be superior.

I. Spray Treatments

A 50:1 mixture of Exxsol D130 (aliphatic hydrocarbon) and Adsee ME 722 (emulsifier) is identified as Sample A. A 10:1 mixture of Epal 12 (dodecanol containing a small amount of tetradecanol) and Adsee ME 722 is identified as Sample B. These samples provided $^{14}$C-uptake of propiconazole similar to BSO's in the greenhouse uptake system. These samples were prepared in large quantities and applied in a field study in Honduras. In this study, both experimental products were successful in maintaining the disease control efficacy of Tilt, with no phytotoxicity interaction with Bravo (Table 2).

TABLE 2

Evaluation of Oil Substitutes

| | |
|---|---|
| 1 | Sample A (3.6 l) + Tilt 25 EC (0.4 l) + water |
| 2 | Sample B (1.1 l) + Tilt 25 EC (0.4 l) + water |
| 3 | Orchex 796 or Spraytex M (5.0 l) + Tilt 25 EC (0.4 l) + Sponto (0.025 l) + water |
| 4 | Bravo 720 (2.0 l) + water |
| 5 | Sample A (3.6 l) + Bravo 720 (2.0 l) + water |
| 6 | Sample B (1.1 l) + Bravo 720 (2.0 l) + water |

*All treatments contained water to a total combined volume of 20.l for application to a 1 hectare plot II. Schedule of Plot Treatments by Application Dates (1995/96)

The treatment of plots #1, #2 and #3 with the samples identified in Table 2 were scheduled as shown in Table 3.

TABLE 3

| Application Date | Treatment No.** Applied* to | | | Notes |
|---|---|---|---|---|
| | Plot #1 | Plot #2 | Plot #3 | |
| Nov. 25 | 1 | 2 | 3 | Plot #3 received Orchex 796 |
| Dec 8 | 1 | 2 | 3 | Plot #3 received Orchex 796 |
| Dec 18 | 4 | 4 | 4 | |
| Dec 27 | 1 | 2 | 3 | Plot #3 received Spraytex |
| Jan 9 | 1 | 2 | 3 | Plot #3 received Spraytex |
| Jan 16 | 4 | 4 | 4 | |
| Jan 23 | 1 | 2 | 3 | Plot #3 received Spraytex |
| Feb 12 | 4 | 4 | 4 | |
| Feb 20 | 5 | 6 | 4 | |

*All applications were made at a total volume rate of 20.0 l/ha.
**Treatment No. from previous table.

III. Experimental Plots

The trials were conducted in non-commercial banana plots adjacent to a commercial banana plantation, Catrachos Farm, Batan, Honduras (FIG. 1). The plots were expansion acreage and consisted of 9-month old banana plants at the initiation of the trial. Cultural practices (pruning, deleafing, fertilization, irrigation) were generally deficient during the course of the trial. See FIG. 1 for a plot layout.

IV. Evaluation

Since plot sizes were small, disease severity data and phytotoxicity data were taken from 30 plants in the center of each plot. These plants were marked with a ribbon and the same plants were used for each evaluation. For evaluation of disease severity, the youngest leaf attacked (YLA) was assessed. A leaf with 10 or more necrotic streaks was considered attacked. Phytotoxicity was assessed by rating leaf #8 on a scale of 0–10, with 10 representing 100% blackening of the leaf and 0 representing no visible blackening of the leaf lamina or midvein (Table 4). Note that in the treatment Plot No. 1, initial YLA was lower than the other two treatments.

TABLE 4

Evaluation of Streaking Caused by Black Sigatoka

| | YLA | | | Functional Leaves/Plant | | |
|---|---|---|---|---|---|---|
| Date | Plot #1 | Plot #2 | Plot #3 | Plot #1 | Plot #2 | Plot #3 |
| 23-11-95 | 4.5 | 4.9 | 4.8 | 7.2 | 8 | 8.4 |
| 30-11-95 | 4.6 | 5.1 | 5.0 | 7.2 | 8.1 | 8.5 |
| 07-12-95 | 5.3 | 5.8 | 5.8 | 7.7 | 8.4 | 8.7 |
| 14-12-95 | 4.9 | 5.5 | 6.1 | 7.4 | 8.5 | 8.5 |
| 22-12-95 | 4.9 | 5.4 | 5.5 | 8.4 | 8.7 | 9.2 |
| 29-12-95 | 5.0 | 5.4 | 5.6 | 8.6 | 8.9 | 9.3 |
| 06-01-96 | 5.8 | 5.6 | 6.1 | 9.7 | 10.2 | 11.1 |
| 13-01-96 | 6.0 | 6.0 | 6.0 | 9.7 | 10.6 | 10.8 |
| 20-01-96 | 6.0 | 5.6 | 6.4 | 10.5 | 10.7 | 11.7 |
| 26-01-96 | 6.3 | 5.8 | 6.4 | 10.5 | 10.8 | 11.7 |
| 01-02-96 | 6.3 | 5.6 | 6.5 | 9.8 | 9.9 | 11.1 |
| 09-02-96 | 6.1 | 5.5 | 6.3 | 8.9 | 9.4 | 11.4 |

The percent (%) change in streaking caused by black sigatoka in the three treatments at the beginning and end of the trial is shown in Table 5.

TABLE 5

Mean YLA (youngest leaf attacked) at the beginning and end of trial

| Treatment | YLA initial | YLA final | % change |
|---|---|---|---|
| A | 4.5 | 6.1 | 35.5 |
| B | 4.9 | 5.5 | 12.2 |
| Orchex | 4.8 | 6.3 | 31.2 |

V. Results

Figure 2:
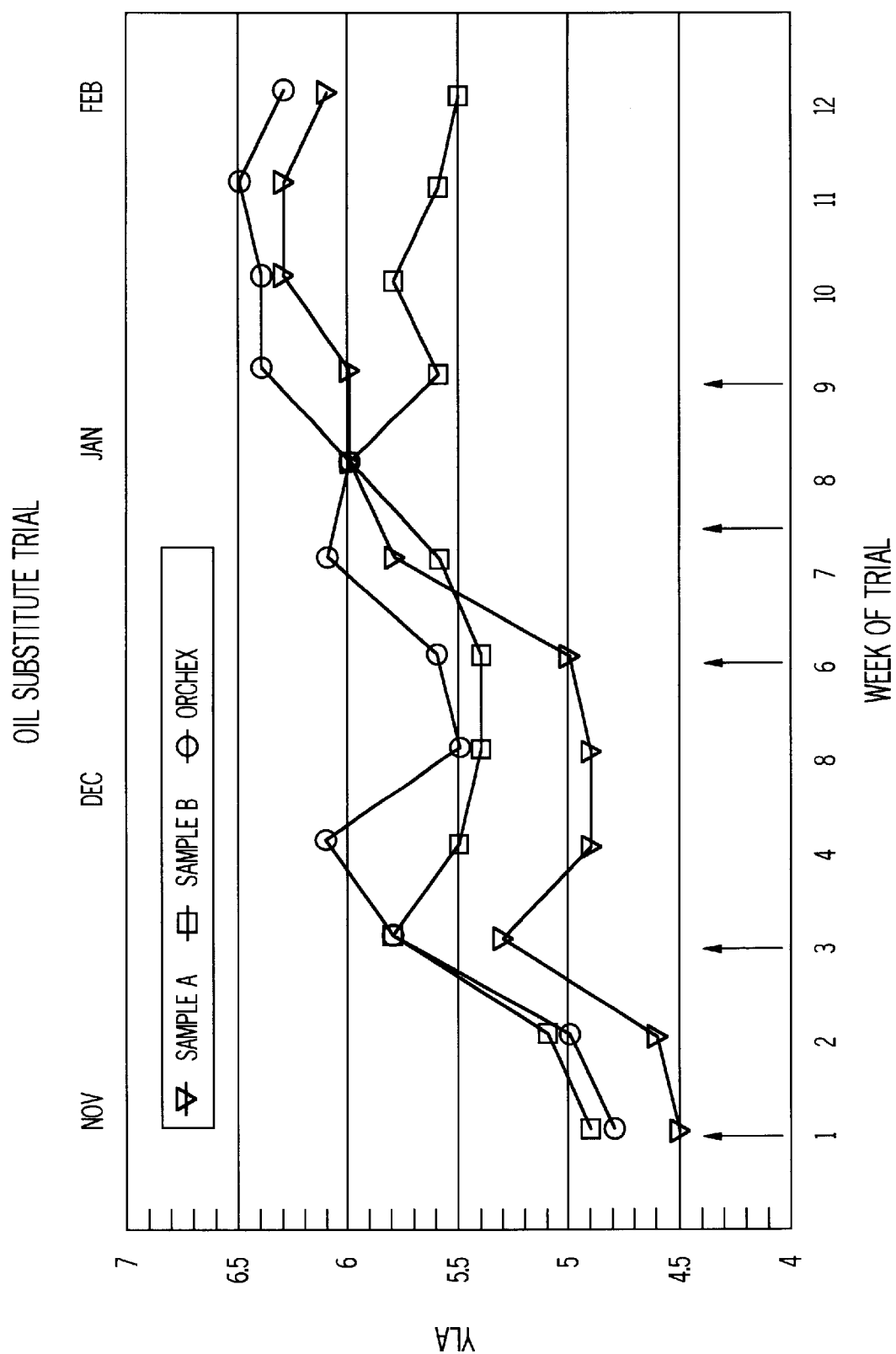

FIG. 2 is a graph showing mean YLA on each rating date for the three treatments. These data indicate that Sample A and Sample B were similar to Orchex in efficacy.

Mean phytotoxicity ratings are shown in Table 6. No phytotoxicity was observed with Sample A or Sample B, even after an application of a Bravo tank mix on Feb. 20, whereas the typical Bravo-oil phytotoxicity symptoms were manifested in Plot No. 3.

TABLE 6

Mean phytotoxicity rating of leaf #8 in 30 plants.

| Date | A | B | Orchex |
|---|---|---|---|
| 11-30-95 | 0.0 | 0.0 | 0.0 |
| 12-20-95 | 0.0 | 0.0 | 2.7 |
| 12-29-95 | 0.0 | 0.0 | 2.4 |
| 1-21-96 | 0.0 | 0.0 | 1.4 |
| 1-28-96 | 0.0 | 0.0 | 1.8 |
| 2-25-96 | 0.0 | 0.0 | — |

Having described the invention in detail and by reference to preferred embodiments thereof, it will be apparent that modifications and variations are possible without departing from the scope of the invention defined in the appended claims.

What is claimed is:

1. A method for reducing the incidence of fungal infection in crops which comprises the steps of:
   (a) applying to a crop an aqueous spray composition which includes a pesticide and a spray adjuvant including a solvent and an emulsifier, wherein the solvent is a mixture of aliphatic hydrocarbons having a distillation range of about 520 to 600° F. and an aromatic content of about 1% by weight or less, or the solvent is one or a combination of $C_6$–$C_{18}$ fatty alcohol(s); and
   (b) applying chlorothalonil to the crop previously to, simultaneously with or subsequently to the application of the aqueous spray composition,
wherein phytotoxic interaction between the spray adjuvant and the chlorothalonil is reduced or eliminated.

2. The method of claim 1 wherein the pesticide is a systemic fungicide.

3. The method of claim 2 wherein the systemic fungicide is a fungicidal triazole, thiophanate methyl, benzimidazole, dicarboximide, phenyl amide, strobilurane, pyrimidine, or imidazole.

4. The method of claim 3:
   (a) wherein the fungicidal triazole is propiconazole, fenbuconazole, hexaconazole, epoxiconazole, or tebuconazole;
   (b) wherein the fungicidal benzimidazole is benomyl, or thiabendazole;
   (c) wherein the fungicidal dicarboximide is iprodione;
   (d) wherein the fungicidal phenyl amide is metalaxyl or mefenoxam;
   (e) wherein the fungicidal strobilurane is azoxystrobin or kresoxim-methyl;
   (f) wherein the fungicidal pyrimidine is fenarimol;
   (g) wherein the fungicidal imidazole is imazilil; or
   (h) thiophanate methyl.

5. The method of claim 1 wherein the solvent is hydrotreated aliphatic petroleum distillate derived from paraffinic or naphthenic crudes, and having a distillation range of about 538 to 599° F.

6. The method of claim 1 wherein the solvent is an isoparaffinic and naphthenic mixture having a distillation range of about 523 to 592° F.

7. The method of claim 1 wherein the solvent is one or more $C_{10}$–$C_{16}$ fatty alcohols, distilling in the range of about 480 to 580° F.

8. The method of claim 7 wherein the solvent is dodecanol.

9. The method of claim 7 wherein the solvent is tetradecanol.

10. The method of claim 7 wherein the solvent is a mixture of about 65 to 75% by volume dodecanol and about 25 to 35% by volume tetradecanol.

11. The method of claim 1 wherein the emulsifier constitutes about 2 to 10% by weight of the adjuvant.

12. The method of claim 7 wherein said emulsifier a nonionic emulsifier.

13. The method of claim 12 wherein said emulsifier additionally includes a soyate ester and an alkoxylated resin.

14. A method for reducing the incidence of fungal infection in crops which comprises the steps of:
   (a) applying to a crop a non-aqueous spray composition which includes a pesticide and a solvent, wherein the solvent is a mixture of aliphatic hydrocarbons having a distillation range of about 520 to 600 ° F. and an aromatic content of about 1% by weight or less, or the solvent is one or a combination of $C_6$–$C_{18}$ fatty alcohol(s); and
   (b) applying chlorothalonil to the crop previously to, simultaneously with or subsequently to the application of the non-aqueous spray composition,
wherein phytotoxic interaction between the solvent and the chlorothalonil is reduced or eliminated.

15. The method of claim 14 wherein the pesticide is a systemic fungicide.

16. The method of claim 15 wherein the systemic fungicide is a fungicidal triazole, thiophanate methyl, benzimidazole, dicarboximide, phenyl amide, strobilurane, pyrimidine, or imidazole.

17. The method of claim 16:
   (a) wherein the fungicidal triazole is propiconazole, fenbuconazole, hexaconazole, epoxiconazole, or tebuconazole;
   (b) wherein the fungicidal benzimidazole is benomyl, or thiabendazole;
   (c) wherein the fungicidal dicarboximide is iprodione;
   (d) wherein the fungicidal phenyl amide is metalaxyl or mefenoxam;
   (e) wherein the fungicidal strobilurane is azoxystrobin or kresoxim-methyl;
   (f) wherein the fungicidal pyrimidine is fenarimol;
   (g) wherein the fungicidal imidazole is imazilil; or
   (h) thiophanate methyl.

18. The method of claim 14 wherein the solvent is hydrotreated aliphatic petroleum distillate derived from paraffinic or naphthenic crudes, and having a distillation range of about 538 to 599° F.

19. The method of claim 14 wherein the solvent is an isoparaffinic and naphthenic mixture having a distillation range of about 523 to 592° F.

20. The method of claim 14 wherein the solvent is one or more $C_{10}$–$C_{16}$ fatty alcohols, distilling in the range of about 480 to 580° F.

21. The method of claim 20 wherein the solvent is dodecanol.

22. The method of claim 20 wherein the solvent is tetradecanol.

23. The method of claim 20 wherein the solvent is a mixture of about 65 to 75% by volume dodecanol and about 25 to 35% by volume tetradecanol.

24. The method of claim 14 wherein said solvent is present in the applied non-aqueous spray in an amount of about 80 to 96% by volume.

* * * * *